US005491756A

United States Patent [19]
Francais

[11] Patent Number: 5,491,756
[45] Date of Patent: Feb. 13, 1996

[54] SYSTEM FOR DELIVERING SOUND TO AND MONITORING EFFECTS ON A FETUS

[76] Inventor: Caramia Francais, 425 S. Catalina Ave. No. 6, Redondo Beach, Calif. 90277

[21] Appl. No.: 143,981

[22] Filed: Nov. 4, 1993

[51] Int. Cl.⁶ .................................................. H04R 1/02
[52] U.S. Cl. ............................................ 381/90; 381/67
[58] Field of Search ................................ 381/25, 67, 90, 381/124, 187–188, 205, 24; 128/775, 662.04, 660.1; 2/104, 115, 338; 450/79–80, 85

[56] References Cited

U.S. PATENT DOCUMENTS

| 4,781,200 | 11/1988 | Baker | 128/670 |
| 4,798,539 | 1/1989 | Henry et al. | 434/319 |
| 4,830,007 | 5/1989 | Stein | 128/421 |
| 4,934,998 | 6/1990 | Thomas, Jr. | 600/27 |
| 5,109,421 | 4/1992 | Fox | 381/90 |

Primary Examiner—Stephen Brinich
Attorney, Agent, or Firm—Robert J. Schaap

[57] ABSTRACT

A system for generating and delivering sound to a fetus or so-called "fetal child" through the mother's abdomen and which also allows for the monitoring of the effects of sound on the fetal child. The system comprises a belt adapted to be worn about the abdomen area of the mother and includes speakers located in the region of the fetal child for imparting sound through the abdomen wall to the fetal child. The speakers are connected to a sound generator, such as a tape recorder or the like. A stethoscope sensor is mounted in and carried by the belt and is also located in juxtaposition to the abdomen in proximity to the fetal child in order to determine the effects of the sounds on the fetal child. The stethoscope sensor is attachably connected to a stethoscope adapted to be worn by the mother or other user.

20 Claims, 3 Drawing Sheets

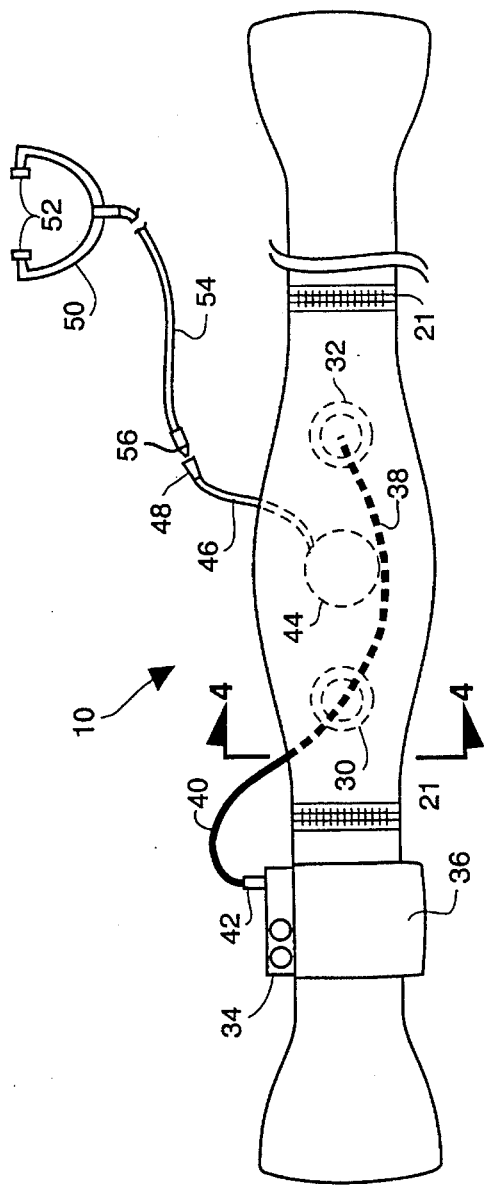
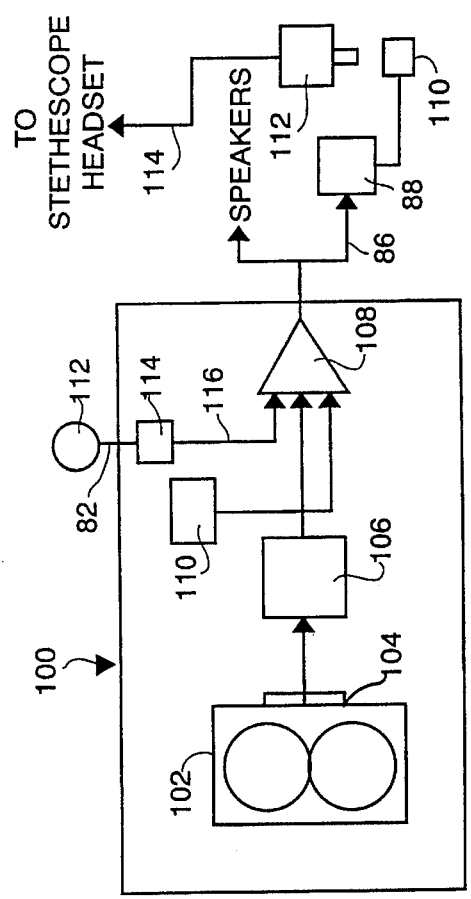
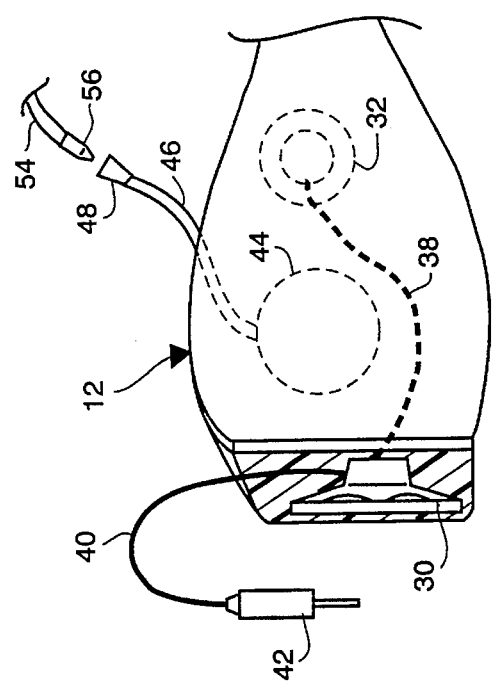

SYSTEM FOR DELIVERING SOUND TO AND MONITORING EFFECTS ON A FETUS

BACKGROUND OF THE INVENTION

1. Field of the Invention

This invention relates in general to certain new and useful improvements in systems for generating and delivering sound to a fetal child through a mother's abdomen and more particularly, to a system of the type stated which also further allows for monitoring of the effects of the sound on the fetal child.

2. Brief Description of the Prior Art

There has been a number of attempts at imparting sounds, such as music and the like, to a fetus while gestating in a mother's abdomen. Usually, these prior art techniques for imparting sound to the fetus rely upon rather basic and unsophisticated arrangements of attempting to place a speaker against the abdomen and holding that speaker against the abdomen when the speaker is connected to a sound generator, such as a radio, a tape player or the like. The problems with this type of prior art arrangement are obvious in that the mother quickly tires of holding the speaker in one hand and the sound generator in the other hand. Moreover, due to the fact that the speakers continuously move, there is not a consistent sound quality imparted to the fetal child.

There have been attempts to attach speakers to a garment in the vicinity of the mother's abdomen. However, here again, these techniques have proven to be relatively unsophisticated and are only temporary arrangements which are not adapted for an effective imparting of sound to a fetal child.

There has been one attempt to impart generated sounds to a fetus during gestation in accordance with U.S. Pat. No. 5,109,421, dated Apr. 28, 1992 entitled "Fetal Speaker System and Support Belt for Maternal Ware." In this prior art arrangement, a belt is provided and contains speakers for imparting sound through the abdomen wall to the fetal child. These speakers are adapted for detachable connection to a sound generating device, such as a tape player, radio or the like. However, the devices taught in the aforesaid U.S. Pat. No. 5,109,421 are partially lacking in certain material respects. In most cases, it has been found that greater support is needed to lift the baby up and off the bladder to provide comfort to the mother and to provide additional support for the lower back.

The belt in the aforesaid U.S. Pat. No. 5,109,421 is of constant overall vertical dimension in its entire circumference around the abdomen of the mother. Thus, it has been found that this is quite lacking in actually providing the needed support.

In addition to the above, it has also been found that the device in the aforesaid U.S. Pat. No. 5,109,421 may also be lacking in that it has no means for monitoring the effects of the sound on the fetal child. It would, of course, be desirable to determine the effect of music or other sounds on at least the respiratory system and circulatory system of the fetal child. However, prior art systems are completely lacking in this respect.

It has been established that it is important to provide a fetal child with some type of soothing music or like sound. Further, since the mother wears the sound generating device and speakers on her abdomen, this creates a greater loving bond between the fetus and the mother. However, and as indicated, substantial support is often needed for many mothers and in addition, it has been found that it would be desirable to monitor the effect of the sound on the fetus.

OBJECTS OF THE INVENTION

It is, therefore, one of the primary objects of the present invention to provide a system for generating and imparting sound to a fetus through the mother's abdomen and which allows for monitoring of the effects on the fetal child.

It is another object of the present invention to provide a system of the type stated which provides for adequate support around the mother's waist or abdomen, so as to maintain the speakers in a uniform position with respect to the fetus.

It is a further object of the present invention to provide a system of the type stated which is relatively simple in its construction and relatively simple in operation.

It is an additional object of the present invention to provide a system for generating and imparting sounds to a fetus of the type stated which is highly reliable in operation but which can, nevertheless, be manufactured at a low unit cost.

With the above and other objects in view, my invention resides in the novel features of form, construction, arrangement and combination of parts presently described and pointed out in the claims.

BRIEF SUMMARY OF THE DISCLOSURE

Generally speaking, the present invention relates to a system for generating and imparting sound to a fetus (often referred to as a "fetal child") through the mother's abdomen and which allows for monitoring of the effects on the fetal child. This system adopts some of the basic principles utilized in U.S. Pat. No. 5,109,421, but constitutes a significant advance thereover in that it solves many of the problems which may have arisen in that prior art system.

The system for generating and imparting sounds of the present invention comprises a belt sized for wearing disposition about the waist of a woman user and having an enlarged frontal portion which extends over a substantial surface area of the lower abdomen of the woman user. This enlarged frontal portion provides for greater support of the entire system itself.

At least one speaker is carried by, and is mounted in this belt. Preferably, a pair of spaced-apart speakers are mounted on and carried on the belt and are located in juxtaposition to the abdomen in proximity to the fetal child. In this way, the speakers can impart sound to the fetal child across the wall of the abdomen.

A sound generator means, as, for example, a radio or so-called "Walkman" unit, such as a tape or compact disc player or the like is also carried by this belt. This sound generator is capable of generating sounds of the type to be imparted to the fetal child and has an output connected to the one or more speakers.

A stethoscope sensor is also mounted in and carried by the belt and further is located in juxtaposition to the mother's abdomen. Again, the stethoscope sensor is located in proximity to the fetal child to enable listening to the sounds generated by the fetal child in the mother's abdomen.

A sound conductor extends from the stethoscope sensor and has a connector for coupling to a stethoscope earpiece so that a user of the system can monitor the effects of the sound on the fetal child. In this case, the stethoscope earpiece would be worn by the user of the system for listening to sounds generated by the fetal child.

In one embodiment of the invention, and its simplest form, the stethoscope sensor is connected to a coupling which connects to another sound tube and which is, in turn, ultimately connected to the head piece used by the user of the system. In this case, the sound which is generated by the fetus is carried directly to the ears of the mother without any electrical attenuation.

In another embodiment of the invention, a separate amplifier system is employed for amplifying the sound generated by the fetus. This sound amplifier system converts the generated sound into an equivalent electrical wave form which is amplified and then reconverted by speakers at the headset into audible sounds for listening by the mother. In still a further embodiment, the amplification system which forms part of the sound generator means, such as the radio or "Walkman" unit, is utilized for amplifying the sound generated by the fetus.

It has been found in connection with the present invention that heart rate, for example, is a function of the sounds which are imparted to the fetus across the abdomen wall. For example, in some cases, the fetus responds more favorably to soft music, where as in other cases, the fetus may respond more favorably to music of a faster beat or the like. In like manner, the mother can also monitor the effects of sound characteristics, such as the treble or bass effects, or the like, on the fetal child. In any case, the system enables the mother to adequately monitor the effects on the fetal child.

It has also been established that the physical activity of the fetal child as, for example, kicking and the like, may be a result of the type of music or other sounds which is imparted to the fetal child. Here again, this is another parameter for determining the effect of the sounds on the fetal child.

This invention possesses many other advantages and has other purposes which may be made more clearly apparent from a consideration of the forms in which it may be embodied. These forms are shown in the drawings forming a part of and accompanying the present specification. They will now be described in detail for purposes of illustrating the general principles of the invention, but it is to be understood that this detailed description, and the accompanied drawings, are not to be taken in a limiting sense.

BRIEF DESCRIPTION OF THE DRAWINGS

Figure 1:
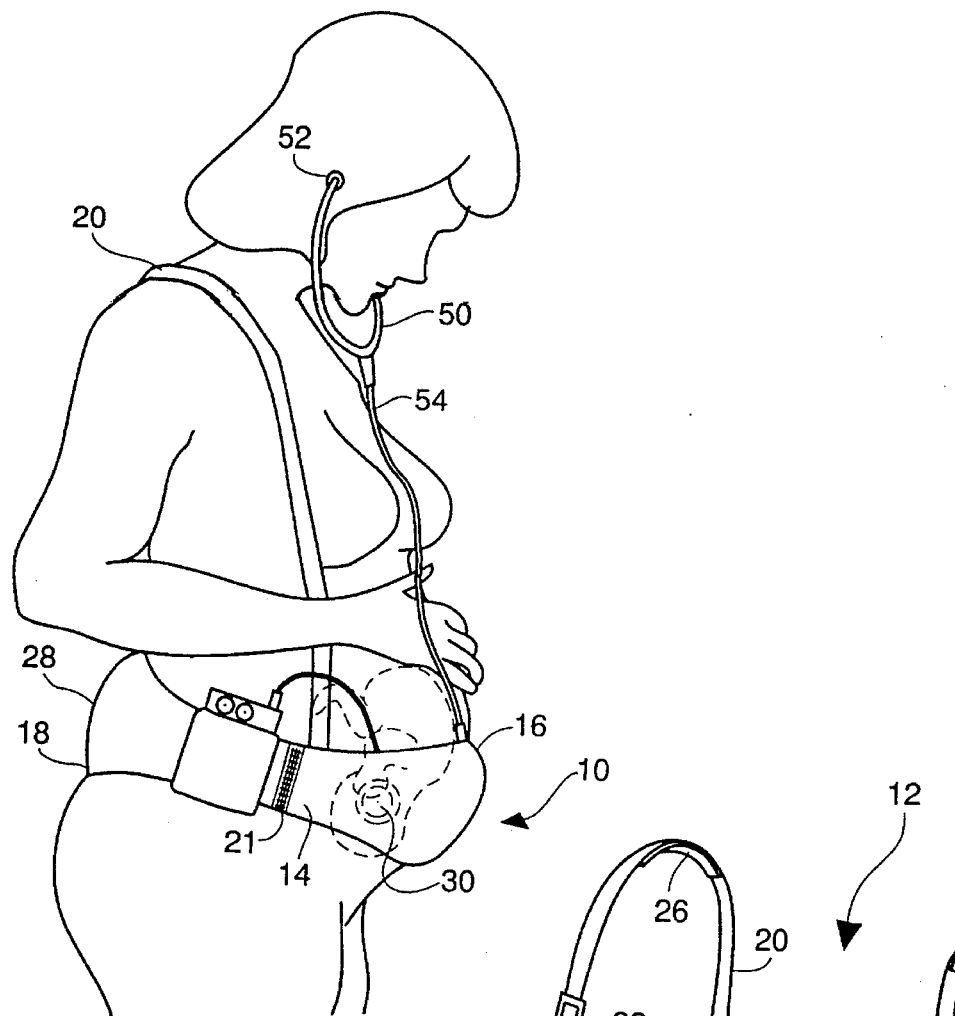
Figure 2:
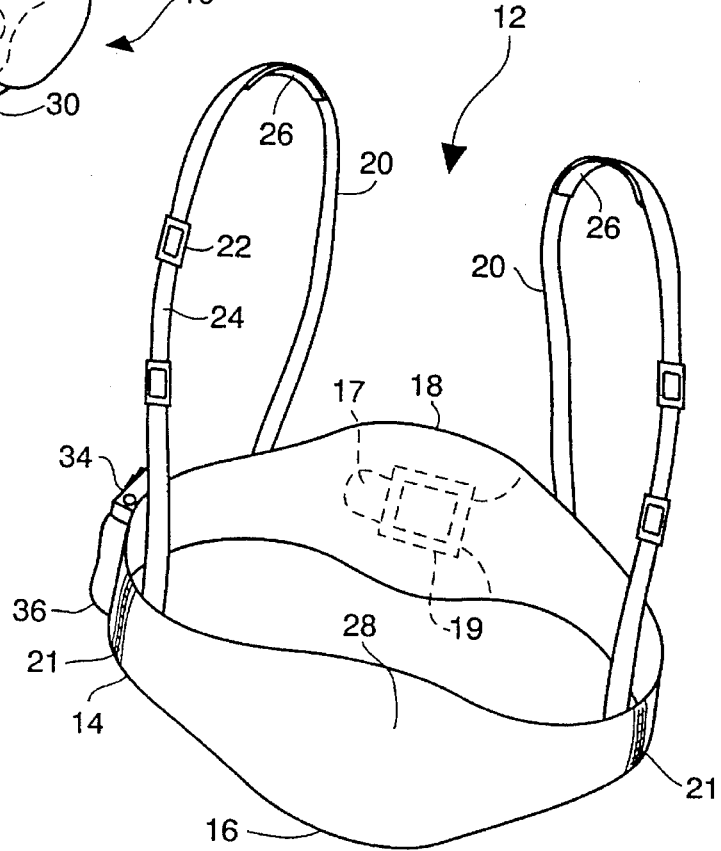
Figure 5:
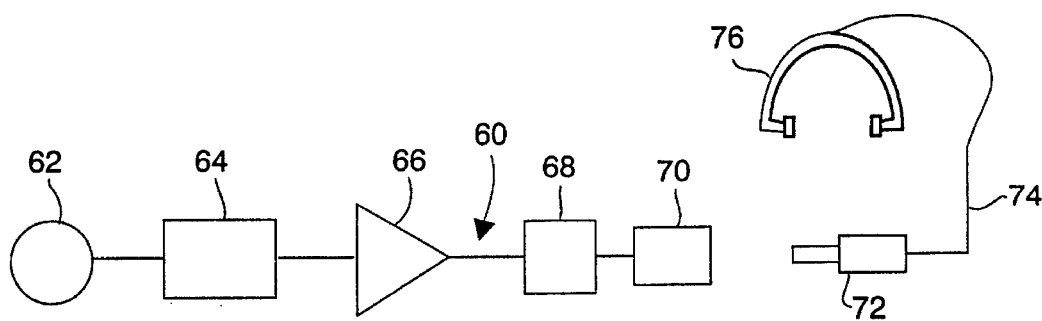
Figure 6:
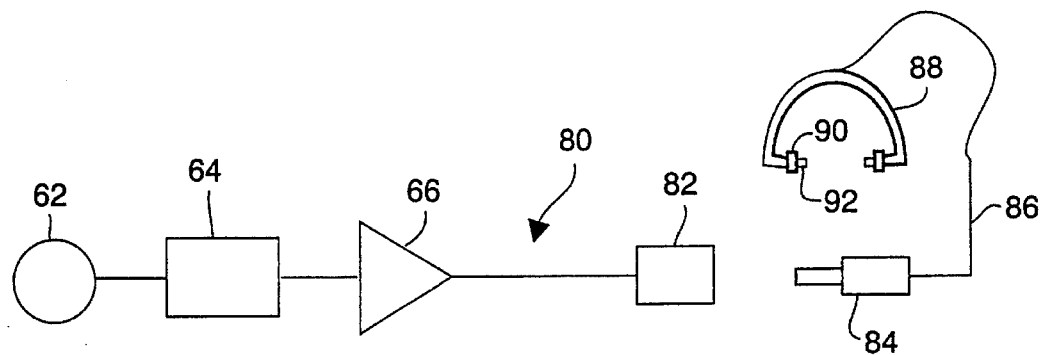

Having thus described the invention in general terms, reference will now be made to the accompanying drawings in which:

FIG. 1 is a perspective view in which the system for generating and imparting sounds to a fetus is used and worn by a mother;

FIG. 2 is a an enlarged perspective view showing the belt and harness arrangement forming part of the system of the present invention;

FIG. 3 is a front elevational view showing the positional arrangement of several of the components forming part of the system for generating and imparting sounds on the belt forming part of the system of the invention;

FIG. 4 is an enlarged fragmentary sectional view showing the operative connection of a speaker located in the belt and a stethoscope monitor in the belt;

FIG. 5 is a schematic view showing one form of system for generating and imparting sounds to a fetal child utilizing an amplification system for amplifying the sounds generated by a fetus;

FIG. 6 is a schematic view, similar to FIG. 5, and showing a modified form of system for amplifying the sounds generated by a fetal child; and FIG. 7 is a schematic view showing still another alternate form of system for generating and imparting sounds to a fetal child and which also utilizes electrical amplification thereof and which is also constructed in accordance with and embodying the present invention.

DETAILED DESCRIPTION OF PREFERRED EMBODIMENTS

Referring now in more detail and by reference characters to the drawings which illustrate several practical embodiments of the present invention, 10 designates a system for generating and imparting sounds to a fetus or so-called "fetal child" through the abdomen wall of the mother. The system 10 comprises a harness arrangement 12 which includes a belt 14 sized to extend around the abdomen of the mother. The belt 14 is constructed so that it has an enlarged frontal section 16 and an enlarged rear section 18.

By reference to FIG. 2, it can be observed that the enlarged frontal section 16 and, for that matter, the enlarged rear section 18, are both enlarged in the sense that they have a greater overall vertical dimension. In this way, it has been found that a belt with non-constant vertical dimension, particularly in the front and rear portions thereof, tends to provide a greater support to the mother who is wearing the harness 12 of the invention. In this case, it has been found that little support is actually provided on the sides and therefore, the sides are of reduced thickness.

In order to facilitate ease of wearing, the belt 14 is provided with a terminal end section 17 which fits within a belt buckle 19. Furthermore, it has been found in connection with the present invention that the terminal section 17 and the buckle 19 should be located at the rear portion of the belt in order to allow for some expansion of the belt as the fetus grows and the mother's abdomen expands. For this purpose, elastic strips 21 may also be formed on the sides of the belt in order to provide some degree of expansion. It should also be understood that other means for adjustably sizing the belt, such as the use of Velcro strips or the like could also be employed. The elastic strips 21 are preferably positioned toward the side of the belt so that they are, in effect, rearward of the speakers. In this way, expansion of the mother's abdomen will not result in a changing of the position of the speakers (hereinafter described) with respect to the fetal child.

In addition to the foregoing, and in order to provide greater support for the mother wearing this harness 12, the harness 12 is provided with a pair of suspender straps 20, as also best illustrated in FIGS. 1 and 2. The suspender straps 20 are also provided with buckles 22 for adjustably sizing the overall length of each of the suspender straps 20. Furthermore, if desired, these suspender straps 20 could be provided with elastic portions 24. These elastic portions 24 also allow for some individual stretching when the mother changes her position.

The suspender straps 20 should be connected to the belt so that they are adjustably securable to the belt at selected positions along the length of the belt. Thus, as the mother's abdomen expands, the belt is opened to a larger loop and the suspender straps can be moved outwardly. For this purpose, a series of buttons or other fasteners may be provided on the belt for releasably securing the lower end of the suspender straps.

The underside of the suspender straps 20, particularly in the shoulder regions, are provided with soft pads in order to provide wearing comfort to the mother. These shoulder pads 26 may be provided of a soft felt-like material so as to reduce the abrasive effect of a conventional pair of straps.

The belt 14 is preferably formed of a leather material, although any other type of material, such as a woven fabric or the like, could be used. Various rubber materials or foam materials could be used. A preferred rubber material which can be used is a neoprene rubber. However, leather is preferred inasmuch as it has some structural integrity and also provides for the necessary rigidity to hold speakers and a sound generator, as hereinafter described. The suspender straps 20 may also be formed of leather although, again, other materials may similarly be employed.

The belt 14 is provided with a buckle 28 for opening and closing the belt 14 in order to position the belt 14 around the waist of the user. Further, the belt 14 and the buckles 28 may be cooperatively designed so as to be adjustable in size. If desired, the belt 14 could also be provided with one or more elastic sections in order to provide some elasticity and thereby allow for movement of the mother, if desired.

The belt 14 is also provided with pockets to receive speakers 30 and 32 and which are, in turn, covered by a thin, flexible cloth-like material. The exact means for mounting the speakers 30 and 32 within the belt 14 is not critical and any conventional mechanism for mounting the speakers 30 and 32 may be employed. In the case of the present invention, the speakers 30 and 32 are fitted within the recesses formed in the belt 14 and project to the interior surface of the belt 14. In this way, the speakers 30 and 32 will be juxtaposed to the wall of the abdomen of the mother when the belt system 10 is worn.

The speakers 30 and 32 are connected to a sound generator 34, such as a conventional radio and tape player combination. The sound generator 34 could also adopt the form only of a tape player, a radio or the like. In a preferred embodiment, the combination radio and tape player, such as the so-called "conventional Walkman" radio/tape playing unit could be employed. This radio/tape player 34 is disposed within a pocket 36 formed on the exterior surface of the belt 14 so as to suitably and removably retain the sound generating unit 34. The speakers and/or amplifier forming part of the player is preferably low volume speakers or amplifier.

The speakers 30 and 32 are internally connected through an electrical conductor located within a plural ply belt structure with the wires connecting the speakers 30 and 32 extending between plys of the belt. The conductor 38 exits the belt 14, as shown at 40 in FIG. 3, and is provided with a plug 42 at its terminal end for detachable connection to the sound generating unit 34. In this way, the sound generating unit 34 can be removed from the belt 14 and used for other purposes. When it is desired to play music or other sounds for the fetal child, the sound generating unit 34 is inserted in the pocket 36 and connected through the plug 42 to the speakers 30 and 32. The remaining operation of the sound generating unit 34 and the generation of electrical signals for creating the sound at the speakers 30 and 32 is conventional and therefore, is neither illustrated nor described in any further detail herein.

Also mounted in a pocket on the interior surface of the belt 14 is a sensor 44 which functions as a stethoscope sensor. Here again, the stethoscope sensor 44 is located close to the interior surface so that it is also disposed in juxtaposed relation to the wall of the abdomen of the mother. Further, a conductor 46 extends from the sensor 44 through the plys forming the belt 14 and terminates in a socket 48, as shown. The present invention provides a conventional stethoscope headset 50 for mother to place in a position where the earpieces 52 are disposed in the ears of the mother. A cable 54 extends from the headset 50 and terminates in a plug 56 which is adapted for detachable connection to the socket 48.

In accordance with the above-identified construction, it can be observed that a user of this system can insert the earpieces 52 of the stethoscope 44 in her ear and connect the plug 56 to the socket 48. In this way, the headset 50 will be in sound conductive relationship with the stethoscope sensor 44.

When the mother desires to monitor the effect of the sounds on the fetal child, the mother can turn off the sound generator 34 and listen to the sounds from the abdomen itself. In this case, the mother may readily hear the heartbeat of the fetal child or otherwise, any physical activity such as kicking and the like. The mother is then in an excellent position to determine the effect of one type of music or other sound upon the fetal child, compared to different music. Thus, the mother can obtain that music or other sound which is most soothing or enjoyable to the fetal child.

The above-identified embodiment of the system is highly effective and relatively inexpensive, since it utilizes a conventional sound generator 34 and an associated stethoscope arrangement. Consequently, it is not necessary to engage in an expensive or elaborate modification of existing components. Nevertheless, the system 10 is highly effective and accomplishes the desired results.

FIG. 5 illustrates an embodiment of the invention which uses a small electrical amplification system 60 for amplifying or otherwise attenuating the sounds generated by the stethoscope sensor. In this case, a stethoscope sensor 62, substantially identical to the previously described sensor 44, is mounted on the belt in substantially in the same position as the sensor 44. The output of the sensor 62 is introduced into a pizzo-electric crystal 64 for converting into an equivalent electrical signal. This electrical signal is then introduced into an operational amplifier 66 where the signal is amplified. In this respect, it should be understood that filters could also be employed for otherwise enhancing the sounds generated by the stethoscope sensor, if desired.

The output of the amplifier 66 is again introduced into another pizzo-electric crystal 68 for conversion back into sound. In this case, the output of the crystal 68, or similar electrical-sound converter, is connected to a coupling 70. The coupling 70 receives a plug 72 and which is connected through a sound tube 74 to a stethoscope headset 76. Thus, amplified sound is delivered directly to the stethoscope headset 76.

The sound amplification system, as illustrated in FIG. 5, is relatively simple, but is effective in amplifying the sounds of the fetus so that they can be more readily understood and heard by a mother who is relatively unexperienced with stethoscope sounds. The amplification system can be in the form of a small chip which can be mounted directly to the belt or otherwise, it can be included in a small compact unit which is affixed to the belt or retained in a pocket on the belt.

FIG. 6 illustrates a slightly modified form of amplification system 80 and which is many ways similar to the amplification system 60. In this case, the amplification system 80 utilizes the stethoscope sensor 62 and the pizzo-electric crystal 64, as well as the amplifier 66, as previously described. The output of the amplifier 66 is retained in the electrical signal form and introduced directly into a female fitting 82 of an electrical connector. A plug 84 is adapted for detachable connection to the fitting 82 and is provided with an electrical signal-carrying conductor 86 connected to a headset 88. In this case, the headset 88 is provided with speakers 90 and associated earpieces 92, as illustrated in FIG. 6. Thus, the electrical signal which is amplified or otherwise attenuated at the amplifier 66 is introduced in the electrical form to the speakers 90 where the signals are thereupon reconverted into sound signals by the speakers 90.

The amplification system of FIG. 6 is also relatively simple in operation and in construction and can also be constructed at a relatively low unit cost. The speakers 90 can also be relatively low cost speakers, since speaker quality is not necessarily required in the system of the present invention.

FIG. 7 illustrates a further embodiment of a system for generating and imparting sound to a fetal child through a mother's abdomen and which also allows for monitoring the effects on the fetal child. In this system, amplification is achieved using the sound generator which is employed for generating the sound imparted to the fetal child. Thus, no separate amplification system is required, although modification of a conventional sound generator may be required in this embodiment of the invention.

In accordance with the embodiment of the invention, as illustrated in FIG. 7, the sound generator 100 is employed and is used for generating sounds and delivering the sounds directly to the speakers, such as the speakers 30 and 32. In this case, the sound generator includes a conventional tape transport 102 containing heads 104. A signal is derived from the heads 104 and is delivered to a signal conditioning circuit 106. This signal conditioning circuit 106 is essentially conventional and includes all of the components normally found in a tape player. The output of the signal conditioning circuit 106 is thereupon introduced into an output amplifier 108 which is normally part of the signal conditioning circuit, but which is separated for purposes of illustration, as also shown in FIG. 7. In addition, the sound generating unit 100 comprises a conventional tuner 110 which similarly has an output to the output amplifier 108.

In the embodiment of the invention, as illustrated in FIG. 7, the amplifier 108 also receives an input from a stethoscope sensor 112 and where the output of the sensor 112 is converted by means of a pizzo-electric crystal 114 into an equivalent electrical signal. This signal from the crystal 114 is carried over an electrical conductor 116 directly to the amplifier 108. In this case, the same amplifier used for generating amplification of the sound for delivery to the fetal child is also used for amplification of the signal from the stethoscope sensor 112.

Inasmuch as it is not necessary to generate sounds for the fetal child simultaneously with monitoring the effects on the fetal child, the sounds which are generated for the fetal child can be temporarily turned off when attempting to monitor. Otherwise, the mother could simultaneously listen to the sounds which are generated along with the sounds created by the fetal child.

The stethoscope sensor 112 is similar to the previously described stethoscope sensors 44 or 62 and operates in the same manner. Again, the stethoscope sensor 112 would also be mounted on or in the belt.

The output of the amplifier 108 is connected to the speakers, such as the speakers 30 and 32, as aforesaid. In like manner, the output of the amplifier 108 is connected to an electrical coupling comprised of a receptacle 110 and a plug 112. In this case, the plug 112 can be connected to speakers (not shown) in a stethoscope headset of the type previously described in FIG. 6. However, it should be understood that the electrical output of the amplifier 108 could be reconverted back into sound and delivered to a conventional stethoscope headset through a sound tube, much in the same manner as described in connection with the embodiment of FIG. 5.

In accordance with the above-identified construction, it can be observed that amplification of the sound generated by the fetal child can be accomplished in any of the three manners illustrated and described herein. Each are quite effective for use in the present invention. The embodiment of FIG. 7 allows for simplification, but at some additional cost since it is necessary to modify an otherwise conventional sound generating unit. In the embodiments of FIGS. 5–7, the signal is electrically amplified for better hearing by the mother.

Thus, there has been illustrated and described a unique and novel system for generating and imparting sound to a fetal child through a mother's abdomen and which thereby fulfills all of the objects and advantages which have been sought. It should be understood that many changes, modifications, variations and other uses and applications will become apparent to those skilled in the art after considering this specification and the accompanying drawings. Therefore, any and all such changes, modifications, variations and other uses and applications which do not depart form the spirit and scope of the invention are deemed to be covered by the invention.

Having thus described the invention, what I desire to claim and secure by Letters Patent is:

1. A system for generating and imparting sound to a fetal child through the mother's abdomen and which allows for monitoring effects on the fetal child, said system comprising:

a) a belt sized for wearing about the waist of a woman user and having a frontal portion which extends over a surface area of the lower abdomen of the woman user;

b) at least one speaker mounted in and carried by said belt and being located in juxtaposition to the abdomen in proximity to that fetal child for imparting sound to the fetal child across the wall of the abdomen;

c) sound generating means carried by said belt and generating sounds of the type to be imparted to said fetal child and having an output connected to said speaker;

d) a stethoscope sensor for generating audible signals mounted in and carried by said belt and also being located in juxtaposition to the abdomen in proximity to the fetal child to enable listening to sounds generated by the fetal child in the abdomen; and e) a conductor extending from said stethoscope sensor and having a connector for quickly releasably coupling to an earpiece so that a user of the system can monitor the effects of the sound generated by the sound generating means on the fetal child.

2. The system for generating and imparting sound of claim 1 further characterized in that said system comprises a suspender arrangement including a pair of straps connected to said belt and sized for extending over the shoulders of the woman user.

3. The system for generating and imparting sound of claim 2 further characterized in that said straps are adjustably sizable to accommodate differently sized users.

4. The system for generating and imparting sound of claim 2 further characterized in that the frontal portion is enlarged relative to said portions of the belt and which frontal portion extends over a substantial surface area of the lower abdomen of the woman user.

5. The system for generating and imparting sound of claim 1 further characterized in that said system comprises a stethoscope headset for use by the woman user and that a cable extending from said headset comprises a mating connector for connection to the connector on said conductor.

6. The system for generating and imparting sound of claim 5 further characterized in that the connector and the mating connector are adapted for quick release plug-in type connection.

7. The system for generating and imparting sound of claim 4 further characterized in that the conductor extending from the stethoscope sensor is a sound conductor for conducting sound from the sensor to the earpiece.

8. The system for generating and imparting sound of claim 4 further characterized in that the conductor extending from a connector to the earpiece is an electrical conductor and said earpiece comprises a speaker for reconverting an electrical signal into equivalent sounds representing the sounds generated by the fetal child.

9. The system for generating and imparting sound of claim 4 further characterized in that said belt has an enlarged rear portion and where both the enlarged frontal portion and enlarged rear portion have a greater vertical dimension then the remaining portions of the belt to provide greater wearing support.

10. The system for generating and imparting sound of claim 4 further characterized a means is provided for converting the sound from the stethoscope sensor and separate amplification means amplifies the converted signal and further means is provided for reconverting the amplified signal back to sound for hearing by the mother.

11. The system for generating sound and imparting sound of claim 4 further characterized in that an amplifier in the sound generating means is used for amplifying the signals from the fetal child.

12. A system for generating and imparting sound to a fetal child through the mother's abdomen and said system comprising:
a) a belt sized for wearing about and completely encircling the waist of a woman user and having a frontal portion which extends over a substantial surface area of the lower abdomen of the woman user;
b) said belt having a rear portion which extends over a substantial surface area of the back of the woman user;
c) said belt further having side portions which connect the frontal portion and the rear portion and where the frontal portion and rear portion are enlarged relative to the side portions and have greater vertical dimensions that the side portions when worn:
d) suspender straps connected to said belt and extending over the shoulder area of a user;
e) at least one speaker mounted in and carried by said belt and being located in juxtaposition to the abdomen on or in proximity to the frontal portion of the belt and in proximity to the fetal child for imparting sound to the fetal child across the wall of the abdomen; and
f) sound generating means carried by said belt in proximity to the front portion thereof and generating sounds of the type to be imparted to said fetal child and having an output connected to said speaker.

13. The system for generating and imparting sound of claim 12 further characterized in that said suspender straps are adjustably sizable to accommodate differently sized users.

14. The system for generating and imparting sound of claim 12 further characterized in that the system further comprises a stethoscope sensor mounted in and carried by said frontal portion of said belt and also being located in juxtaposition to the abdomen in proximity to the fetal child and having a connector for coupling to a stethoscope earpiece so that a user of the system can monitor the effects of the sound on the fetal child.

15. The system for generating and imparting sound of claim 14 further characterized in that said system comprises a stethoscope headset for use by the woman user and that a cable extending from said headset comprises a mating connector for connection to the connector on said conductor.

16. The system for generating and imparting sound of claim 15 further characterized in that the connector and the mating connector are adapted for quick release plug-in type connection.

17. A system for generating and imparting sound to a fetal child through the mother's abdomen and which allows for monitoring effects on the fetal child, said system comprising:
a) a belt sized for wearing about the waist of a woman user and having a frontal portion which extends over a surface area of the lower abdomen of the woman user;
b) at least one speaker mounted in and carried by said belt and being located in juxtaposition to the abdomen in proximity to that fetal child for imparting sound to the fetal child across the wall of the abdomen;
c) sound generating means carried by said belt and generating sounds of the type to be imparted to said fetal child and having an output connected to said speaker;
d) a conductor connecting said sound generating means to said speaker and extending along and through said belt, said conductor having an end projecting through said belt in proximity to said sound generating means;
e) a plug on the end of said conductor for connection to said sound generating means;
f) a stethoscope sensor for generating audible signals mounted in and carried by said belt and also being located in juxtaposition to the abdomen in proximity to the fetal child to enable listening to sounds generated by the fetal child in the abdomen;
g) a stethoscope conductor extending from said stethoscope sensor and carrying audible sound detected by said sensor; and
h) a connector for quickly releasably coupling the stethoscope conductor to an earpiece of the use so that a user of the system can monitor the effects of the sound generated by the sound generating means on the fetal child.

18. The system for generating and imparting sound of claim 17 further characterized in that said system comprises a stethoscope headset for use by the woman user and that a cable extending from said headset comprises a mating connector for connection to the connector on said conductor.

19. The system for generating and imparting sound of claim 18 further characterized in that the headset includes said earpiece, and the conductor extending from the connector to the earpiece is an electrical conductor and said earpiece comprises a speaker for reconverting an electrical signal into equivalent sounds representing the sounds generated by the fetal child.

20. The system for generating and imparting sound of claim 18 further characterized a means is provided for converting the sound from the stethoscope sensor and separate amplification means amplifies the converted signal and further means is provided for reconverting the amplified signal back to sound for hearing by the mother.

* * * * *